United States Patent [19]

Holman et al.

[11] 4,422,759

[45] Dec. 27, 1983

[54] PHOTOGRAPHIC ACCESSORY

[76] Inventors: Daniel G. Holman, 12743 Radisson Rd. NE., Blaine, Minn. 55434; Robert A. Ersek, 2300 Cypress Point West, Austin, Tex. 78746

[21] Appl. No.: 260,078

[22] Filed: May 4, 1981

[51] Int. Cl.³ .............................................. G01J 1/02
[52] U.S. Cl. ................................... 356/243; 356/421
[58] Field of Search ....................... 356/404, 421–425, 356/243; 354/62, 100, 105, 109; 33/483–485; 128/1 R; 430/357–359; 355/40

[56] References Cited

U.S. PATENT DOCUMENTS 3,162,533  12/1964  De Pelsmaker et al. ....... 430/357 X

OTHER PUBLICATIONS

Reprorama No. 10, International Bulletin for Graphic Information, Gevaert Photo-Producten, N.V., Antwerp, Belgium (1959).
*Life Library of Photography—Color,* by the editors of Time-Life Books, Time-Life Books, New York, 1970, pp. 126-128.
Huck et al., *Applied Optics,* vol. 15, No. 7, Jul. 1976, pp. 1748-1766.

*Primary Examiner*—F. L. Evans
*Attorney, Agent, or Firm*—Orrin M. Haugen; Thomas J. Nikolai

[57] ABSTRACT

A photographic accessory, for application to a body surface and other medical and scientific uses, having dimensional graduations and color patches to facilitate correlation of photographic data with the actual size and color of the surface in question.

3 Claims, 2 Drawing Figures

PHOTOGRAPHIC ACCESSORY

FIELD OF THE INVENTION

This invention relates to the field of medical photography, and particularly to a photographic accessory of special interest to plastic surgeons.

BACKGROUND OF THE INVENTION

In the treatment of lesions and traumas by plastic surgeons it is very desirable to have running records of the progress of the treatment. Any dimensional changes during treatment are significant, and the color of the parts being treated is also very significant.

Photographic records are kept of the various stages of the treatment, but while they are helpful in the dimensional aspects, they have some deficiency as to color, because of the unavoidable affects of photographics films and processes. A change in color between two successive photographs may not truly represent an actual change in color of the parts in question.

SUMMARY OF THE INVENTION

The present invention comprises an accessory for general scientific and medical use, which may for example be adhered to the body of a patient in the area being treated, and which has not only a dimensional scale but also patches of standard colors. The colors of a photograph taken to include the accessory, when developed, present areas of color which the surgeon can compare with the standard colors themselves, and thus the nature and extent of photographic color degradation may easily be appreciated.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there is illustrated and described a preferred embodiment of the invention.

DESCRIPTION OF THE PREFERRED EMBODIMENT

Figure 1:
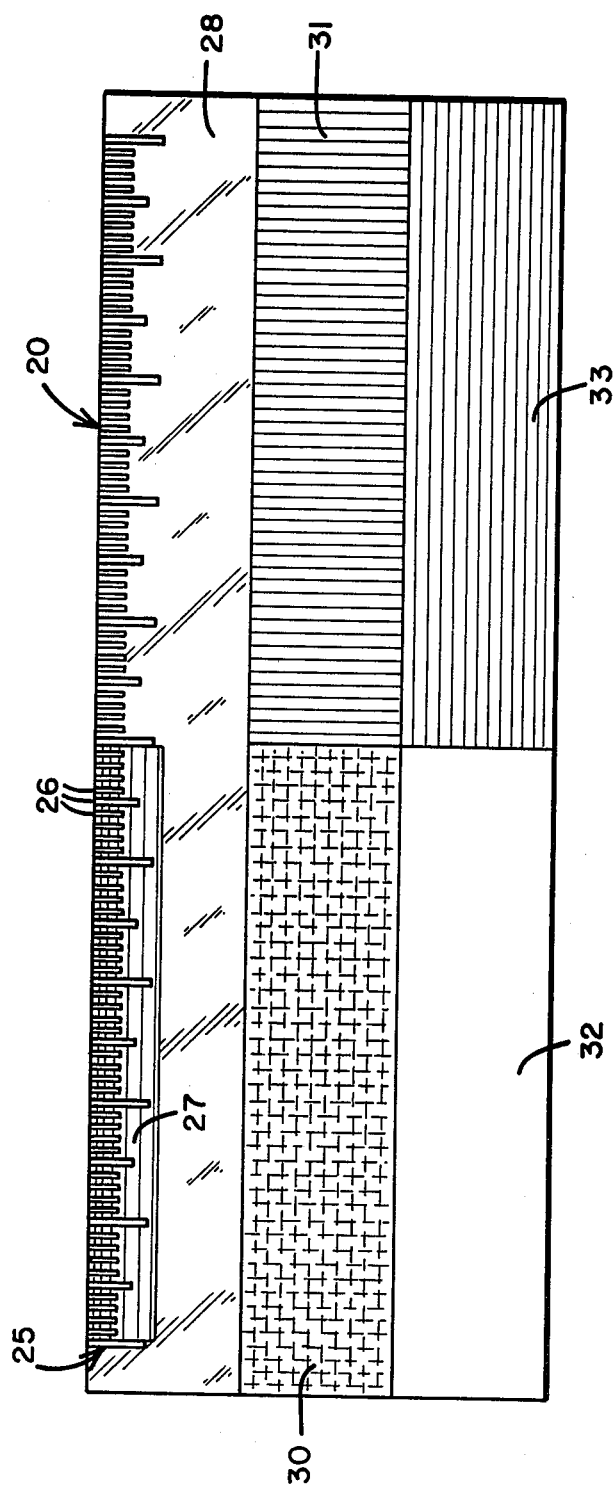
FIGS. 1 and 2 of the drawing are top and end views of an accessory according to the invention, important differences in color being indicated by the standard cross-hatchings for the colors used.
Figure 2:
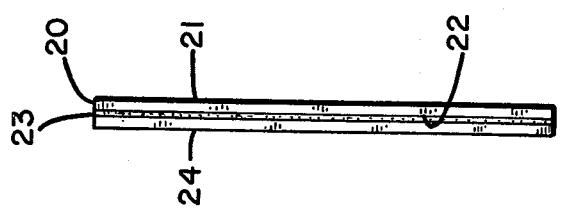

An accessory according to the invention comprises a small sheet 20 of flexible, colorless, translucent material having a front surface 21 with a dull finish. The back surface has a layer 22 of transparent, colorless, pressure-sensitive adhesive 23 protected by an overlay strip 24 which may be peeled therefrom. A graduated scale 25 is formed along one edge of the sheet, in such a manner as to be photograhically perceptible, as by having individual graduations 26 chromatically contrasting with a pair of backgrounds 27 and 28. For example, the graduations may be white, half the background being blue and the other half being colorless and transparent to reveal the color of the surface below the sheet.

Also formed on the front surface of the sheet are a plurality of opaque patches 30, 31, 32, 33 of different colors, as for example the three P.M.S. primary colors and white. The patches do not alter the matte or non-specular reflective characteristics of the front surface. These colors are chromatically standard and uniform throughout the printing industry, and can always be reproduced when needed.

In use the overlay strip is peeled from the back surface of the accessory, which is then adhered to the patient's body so the scale 25 is generally aligned with a major dimension of the area of interest. Circumstances may be such that the accessory is preferably so positioned that the lesion itself is under the translucent portion 20, as the accessories are supplied in sterile state, sealed in protective envelopes, and so may be applied even over an open wound. Photographs of the area being treated are then taken, preferably using color film, after which the accessory is removed and discarded.

When the photograhic prints are received, the color portions thereof can be compared with specimens of the standard colors, and any deviations can be noted and allowed for in the treatment record of the case.

Even if black-and-white photographic techniques are used, the accessory is of value, as the surgeon quickly becomes aware of the relation between changes in the photographically reproduced patterns and deviations from the true colors of the accessory.

From the above it will be evident that the invention comprises an accessory having general scientific and medical use, particularly for facilitating the recording of medical treatments and the later interpretation of the records, particularly as to the colors involved.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

We claim:

1. A photographic accessory for scientific and medical use comprising, in combination:
   a sheet of flexible, colorless, translucent material having a front surface with a dull finish and at least one linear edge having a scale of photographically perceptible graduations along said edge;
   a pressure-sensitive adhesive on the rear surface of said sheet;
   a plurality of opaque patches of primary Printing Manufacturing Standards colors on the front surface of said sheet;
   so that when said sheet is adhered to a body surface at an area to be treated and photographed, observation of the patches in the resultant photograh enables determination of the color of the area, regardless of color deviations introduced by photographic processes.

2. An accessory according to claim 1 in which said graduations are on and distinguishable from a plurality of photographically distinguishable backgrounds.

3. An accessory according to claim 1 in which one of said patches is white.

* * * * *

UNITED STATES PATENT AND TRADEMARK OFFICE
CERTIFICATE OF CORRECTION

PATENT NO. : 4,422,759

DATED : December 27, 1983

INVENTOR(S) : Daniel G. Holman, et al

It is certified that error appears in the above-identified patent and that said Letters Patent are hereby corrected as shown below:

Title Page, Column 1, Line 2, add the following inventor:
-- Arthur A. Beisang, 2263 Dellwood, Roseville, Minn. 55113 --

Signed and Sealed this

Ninth Day of October 1984

[SEAL]

Attest:

GERALD J. MOSSINGHOFF

Attesting Officer

Commissioner of Patents and Trademarks